US012624324B2

(12) United States Patent
Ogura et al.

(10) Patent No.: US 12,624,324 B2
(45) Date of Patent: May 12, 2026

(54) CELL PRESERVATION OR TRANSPORTATION INSTRUMENT AND CELL TRANSPORTATION METHOD

(71) Applicant: FUJIFILM Corporation, Tokyo (JP)

(72) Inventors: Izumi Ogura, Ashigarakami-gun (JP); Keiji Shigesada, Ashigarakami-gun (JP); Shinji Mima, Ashigarakami-gun (JP); Yuki Imakura, Ashigarakami-gun (JP); Shun Goto, Ashigarakami-gun (JP); Nao Yamazaki, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 963 days.

(21) Appl. No.: 17/742,123

(22) Filed: May 11, 2022

(65) Prior Publication Data

US 2022/0267704 A1 Aug. 25, 2022

Related U.S. Application Data

(63) Continuation of application No. PCT/JP2020/042437, filed on Nov. 13, 2020.

(30) Foreign Application Priority Data

Nov. 14, 2019 (JP) ................................. 2019-205944

(51) Int. Cl.
*C12M 1/04* (2006.01)
*C12M 1/00* (2006.01)
*C12M 1/12* (2006.01)

(52) U.S. Cl.
CPC ............ *C12M 23/24* (2013.01); *C12M 23/26* (2013.01); *C12M 37/00* (2013.01)

(58) Field of Classification Search
CPC ....... C12M 23/24; C12M 23/26; C12M 37/00
(Continued)

(56) References Cited

U.S. PATENT DOCUMENTS 5,858,770 A 1/1999 Perlman
2004/0032093 A1* 2/2004 Razavi ................ B01L 3/50853
277/628

(Continued)

FOREIGN PATENT DOCUMENTS

EP 3546561 A1 10/2019
JP 10-52178 A 2/1998
(Continued)

OTHER PUBLICATIONS

Notification of Reasons for Refusal dated Mar. 7, 2023 from the Japanese Patent Office in Japanese application No. 2021-556174.
(Continued)

*Primary Examiner* — Jennifer M.H. Tichy
(74) *Attorney, Agent, or Firm* — Sughrue Mion, PLLC

(57) ABSTRACT

An object of the present invention is to provide a transportation instrument and a transportation method that enable transportation by using a cell culture container as it is. Further, an object of the present invention is to provide a transportation instrument and a transportation method that enable supply of oxygen required for respiration of cells. Further, an object of the present invention is to provide a transportation instrument and a transportation method that enable suppression of migration of a culture medium into and out of cells caused by the influence of an increase in internal pressure with respect to the temperature during transportation. According to the present invention, provided is a cell preservation or transportation instrument including a plurality of cell storage containers, a plate which has a plurality of recesses for holding the plurality of cell storage
(Continued)

containers therein, and a flexible material sheet which seals upper opening portions of the plurality of cell storage containers and upper side wall portions formed by side walls of the recesses of the plate and allows ventilation between an inside and an outside of the plurality of cell storage containers.

12 Claims, 11 Drawing Sheets

(58) Field of Classification Search
   USPC .......................................................... 435/383
   See application file for complete search history.

(56) References Cited

U.S. PATENT DOCUMENTS

| | | |
|---|---|---|
| 2014/0302602 A1 | 10/2014 | Kawasaki |
| 2015/0231628 A1 | 8/2015 | Nozaki et al. |
| 2019/0185799 A1 | 6/2019 | Katou et al. |
| 2019/0225926 A1 | 7/2019 | Katou et al. |
| 2019/0382703 A1 | 12/2019 | Katayama et al. |
| 2020/0370020 A1 | 11/2020 | Matsunaga et al. |
| 2021/0155886 A1 | 5/2021 | Schober et al. |

FOREIGN PATENT DOCUMENTS

| | | |
|---|---|---|
| JP | 2005-295825 A | 10/2005 |
| JP | 2013-128457 A | 7/2013 |
| JP | 2013-128458 A | 7/2013 |
| JP | 5982492 B2 | 8/2016 |
| WO | 2013/094370 A1 | 6/2013 |
| WO | 2017/221665 A1 | 12/2017 |
| WO | 2018/003073 A1 | 1/2018 |
| WO | 2018/079793 A1 | 5/2018 |
| WO | 2019/114996 A1 | 6/2019 |
| WO | 2019/156200 A1 | 8/2019 |

OTHER PUBLICATIONS

International Search Report dated Jan. 19, 2021 in International Application No. PCT/JP2020/042437.
Written Opinion of the International Searching Authority dated Jan. 19, 2021 in International Application No. PCT/JP2020/042437.
International Preliminary Report on Patentability dated May 17, 2022 in International Application No. PCT/JP2020/042437.
Extended European Search Report issued Dec. 5, 2022 in European Application No. 20887324.0.

\* cited by examiner

CELL PRESERVATION OR TRANSPORTATION INSTRUMENT AND CELL TRANSPORTATION METHOD

CROSS-REFERENCE TO RELATED APPLICATIONS

This application is a Continuation of PCT International Application No. PCT/JP2020/042437 filed on Nov. 13, 2020, which claims priority under 35 U.S.C § 119(a) to Japanese Patent Application No. 2019-205944 filed on Nov. 14, 2019. Each of the above application(s) is hereby expressly incorporated by reference, in its entirety, into the present application.

BACKGROUND OF THE INVENTION

1. Field of the Invention

The present invention relates to a cell preservation or transportation instrument and a cell transportation method.

2. Description of the Related Art

After cells are cultured in a business site using a plurality of cell storage containers (also referred to as cell culture inserts) and a plate having a plurality of recesses (also referred to as a well plate) for holding the plurality of cell storage containers therein, the cultured cells may be transported to other business sites or other uses. In the related art, it is common to take out cell culture inserts containing cultured cells from a well plate, transfer the cell culture inserts to an instrument consisting of a dedicated container and a silicone cap, and transport the instrument in a state where the container is filled with a culture medium. However, since the cells are used by taking out the cell culture inserts containing the cells from the instrument and returning the cell culture inserts to a well plate by a recipient of the cells after transportation, the cells may be damaged during the procedure and the risk of contamination increases. Further, as a method of transporting cells in a state where cell culture inserts containing cultured cells are held by a well plate, a method of transporting cells by sealing opening portions of cell culture inserts with a film provided with a pressure sensitive adhesive or seal tape has been used, but there is a problem in that the culture medium (liquid) in the well leaks to the outside.

JP2013-128458A and JP5982492B describe a packaging container for storing a cell culture insert. It is described that a lid portion of the packaging container can be configured to have an elastic member such as silicone or rubber in order to prevent leakage of a culture medium in the container. However, the cell culture insert is required to be taken out from the packaging container and returned to a well plate to culture the cells again after transportation using such a packaging container as described above, and thus various problems of damage to the cells during the procedures and the like occur.

The pamphlet of WO2018/003073A describes a storage container storing a culture container (which is not a cell culture insert) of cells while the culture container, a cover that covers an upper edge portion of the culture container, a pressing member, and a cushioning material are pressed from above and below in a state of overlapping each other. However, since this storage container cannot be transported in a state where a cell culture insert containing cultured cells is held by a well plate, a recipient needs to transfer the cells to culture the cells in a cell culture insert, and thus various problems may still occur.

SUMMARY OF THE INVENTION

In a case where cultured cells are transported, the cells are required to be transported with a culture medium (liquid) that supplies necessary nutrients and oxygen in order to transport the cells in a living state. For this purpose, transportation needs to be carried out by suppressing leakage of the culture medium in the well to the outside and enabling supply oxygen required for respiration to the inside of the cell storage container from the outside.

A first object to be achieved by the present invention is to provide a cell preservation or transportation instrument and a cell transportation method that enable cell transportation by using a cell culture container as it is.

A second object to be achieved by the present invention is to provide a cell preservation or transportation instrument and a cell transportation method that enable supply of oxygen required for respiration of cells during transportation of cells.

A third object to be achieved by the present invention is to provide a cell preservation or transportation instrument and a cell transportation method that enable suppression of migration of a culture medium considered to be caused by the influence of an increase in internal pressure with respect to the temperature during transportation of cells.

As a result of intensive examination conducted by the present inventors in order to achieve the above-described objects, it was found that the above-described objects can be achieved by configuring a cell preservation or transportation instrument with a cell storage container, a plate which has a recess for holding the cell storage container therein, and a flexible material sheet which seals an upper opening portion of the cell storage container and an upper side wall portion formed by a side wall of the recess of the plate and is capable of ventilating the inside and outside of the cell storage container. According to an aspect of the present invention, the following inventions are provided.

<1> A cell preservation or transportation instrument comprising: a plurality of cell storage containers; a plate which has a plurality of recesses for holding the plurality of cell storage containers therein; and a flexible material sheet which seals upper opening portions of the plurality of cell storage containers and upper side wall portions formed by side walls of the recesses of the plate and allows ventilation between an inside and an outside of the plurality of cell storage containers.

<2> The cell preservation or transportation instrument according to <1>, in which the flexible material sheet includes a flexible material sheet main body on a side of the cell storage containers and an expiration sheet having a ventilation property on a side opposite to the side of the cell storage containers, the flexible material sheet main body has holes for ventilation between the inside and the outside of the plurality of cell storage containers, and the expiration sheet has waterproofness with a water repellency of 5 kPa or greater in conformity with JIS L 1092 and a ventilation property with a Gurley air permeability of 30 sec/100 cm$^3$ or less in conformity with TAPPI T460.

<3> The cell preservation or transportation instrument according to <2>, in which a diameter of each of the holes provided on the flexible material sheet main body is in a range of 1 mm to 8 mm.

<4> The cell preservation or transportation instrument according to <2> or <3>, in which the holes of the flexible material sheet main body are provided such that (1) at least one hole is provided inside the opening portion of the cell storage container, and (2) at least one hole is provided outside the upper opening portion of the cell storage container and inside an upper opening portion of the recess of the plate by which the cell storage container is held.

<5> The cell preservation or transportation instrument according to <2> or <3>, in which the holes of the flexible material sheet main body are provided such that at least one hole is provided to straddle between (1) the inside the opening portion of the cell storage container and (2) the outside the upper opening portion of the cell storage container and the inside an upper opening portion of the recess of the plate by which the cell storage container is held.

<6> The cell preservation or transportation instrument according to any one of <1> to <5>, in which the flexible material sheet or a flexible material sheet main body is a gel sheet.

<7> The cell preservation or transportation instrument according to any one of <1> to <6>, in which the flexible material sheet or a flexible material sheet main body has an Asker C hardness of 40 degrees or less in conformity with JIS K 7312.

<8> The cell preservation or transportation instrument according to any one of <1> to <7>, in which the flexible material sheet or a flexible material sheet main body has a thickness of 1 mm or greater and 5 mm or less.

<9> The cell preservation or transportation instrument according to any one of <1> to <8>, in which a bottom portion of the cell storage container is formed of a film having micropores.

<10> The cell preservation or transportation instrument according to any one of <1> to <9>, further comprising: a holding member which holds the plurality of cell storage containers, the plate, and the flexible material sheet in a state of compression in a thickness direction.

<11> The cell preservation or transportation instrument according to <10>, in which the holding member includes a set of pressing plates and a plurality of bolts.

<12> The cell preservation or transportation instrument according to <10>, in which the holding member includes an outer storage container, an outer storage container upper lid, and a crimp locking unit that crimps and locks the outer storage container and the outer storage container upper lid.

<13> A cell transportation method comprising: transporting the cell preservation or transportation instrument according to any one of <1> to <12>, in which cells are stored in at least some of the plurality of cell storage containers.

According to the cell preservation or transportation instrument of the present invention and the cell transportation method of the present invention, it is possible to carry out preservation or transportation by using the cell culture container as it is.

According to the cell preservation or transportation instrument of the present invention and the cell transportation method of the present invention, it is possible to supply oxygen required for respiration of cells during transportation of cells.

According to the cell preservation or transportation instrument of the present invention and the cell transportation method of the present invention, it is possible to suppress migration of a culture medium that is considered to be caused by the influence of an increase in internal pressure during transportation of cells.

DESCRIPTION OF THE PREFERRED EMBODIMENTS

Figure 1:
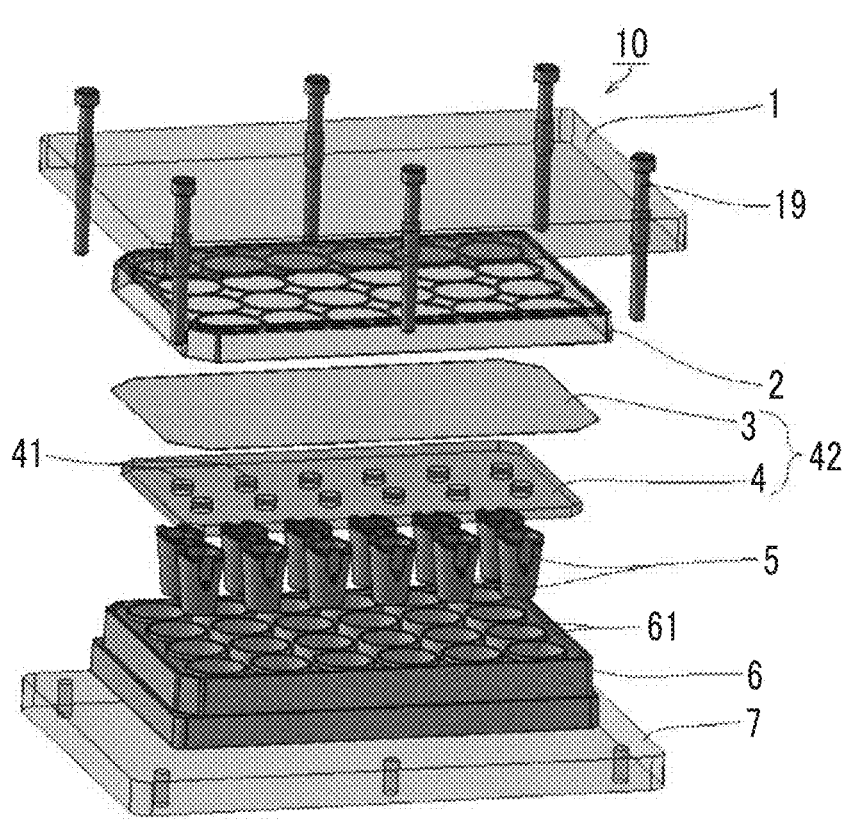
FIG. 1 is a developed perspective view schematically illustrating an embodiment of a cell preservation or transportation instrument of the present invention.

Embodiments of the present invention will be described below.

The present invention relates to a cell preservation or transportation instrument including a plurality of cell storage containers, a plate which has a plurality of recesses for holding the plurality of cell storage containers therein, and a flexible material sheet which seals upper opening portions of the plurality of cell storage containers and upper side wall portions formed by side walls of the recesses of the plate and allows ventilation between the inside and the outside of the plurality of cell storage containers.

Examples of conditions necessary for transportation while maintaining the cell activity include (1) a condition that the culture medium does not come out of the plate even in a case where transportation vibration occurs; (2) a condition that oxygen consumed by cells can be supplemented from the outside; and (3) a condition that the culture medium inside and outside cells does not migrate through a polyethylene terephthalate (PET) film.

According to the cell preservation or transportation instrument according to the embodiment of the present invention, cells can be preserved and transported in a state where the above-described conditions are satisfied.

The effects of the present invention are as described above, and the secondary advantages on the application are as follows. Commercially available cell transportation instruments tend to be expensive, and transportation of cells using commercially available cell culture containers as they are has been virtually impossible. According to the present invention, transportation of cells can be performed using relatively inexpensive commercially available cell culture containers by improving such a situation. Further, the work of the person who delivers cells and the work of the person who receives the cells can be simplified by using the cell culture containers as they are. Specifically, since replacement of cells is not required, the influence during the procedure and the risk of contamination can be significantly reduced. Further, damage to the cells during transportation can be reduced.

[Cell Storage Container]

The cell preservation or transportation instrument according to the embodiment of the present invention includes a plurality of cell storage containers. Here, the term "plurality" is not particularly limited as long as the number thereof is 2 or more, but the number is preferably 4 or more and 100 or less, more preferably 8 or more and 50 or less, and particularly preferably 12 or more and 40 or less.

The cell storage container is not particularly limited as long as the container can store cells, and a container having a function of culturing cells therein is preferable. As the cell storage container, for example, a cell culture container also referred to as a cell culture insert may be used. The shape of the cell storage container is not particularly limited, and examples thereof include a substantially cylindrical container. From the viewpoint of culturing cells, it is preferable that a resin film that is porous for fixation of cells and allows a culture medium to flow is disposed on the bottom portion of the container. It is preferable that the bottom portion of the cell storage container is formed of a film having micropores. The pore diameter of the micropores is not particularly limited.

In a cell storage container having a substantially cylindrical shape, the equivalent circle diameter of the opening portion is preferably 3 mm or greater and more preferably 10 mm or greater. The upper limit thereof is practically 35 mm or less.

[Plate]

The cell preservation or transportation instrument according to a preferred embodiment of the present invention includes a plate having a plurality of recesses for holding the plurality of cell storage containers therein. Here, the term "plurality" is not particularly limited as long as the number thereof is 2 or more, but the number is preferably 4 or more and 100 or less, more preferably 8 or more and 50 or less, and particularly preferably 12 or more and 40 or less.

It is preferable that the recess of the plate (also referred to as a well plate) is formed such that the cell storage container can be stored therein. For this reason, it is preferable that the opening portion of the recess of the well plate has a diameter greater than the diameter of the opening portion of the cell storage container. Specifically, the diameter of the opening portion of the recess is greater than the equivalent circle diameter of the opening portion of the cell storage container preferably by 2 mm and more preferably by 5 mm. The upper limit thereof is not particularly limited, but is practically +20 mm or less with respect to the equivalent circle diameter of the opening portion of the cell storage container. It is preferable that the depth of the recess of the plate is a dimension that enables storage of the cell storage container. The depth of the recess is preferably 2 mm or greater and more preferably 5 mm or greater than the depth of the cell storage container. The upper limit thereof is not particularly limited, but is practically +20 mm or less with respect to the depth of the cell storage container. In terms of the specific dimensions, the opening diameter of the opening portion of the recess in the well plate is preferably 4 mm or greater and more preferably 15 mm or greater. The upper limit thereof is practically 40 mm or less. The depth of the well is preferably 4 mm or greater and more preferably 15 mm or greater. The upper limit thereof is practically 30 mm or less.

[Flexible Material Sheet]

The cell preservation or transportation instrument according to the embodiment of the present invention includes a flexible material sheet which seals upper opening portions of the plurality of cell storage containers and upper side wall portions formed by side walls of the recesses of the plate and allows ventilation between the inside and the outside of the plurality of cell storage containers.

It is preferable that the flexible material sheet includes a flexible material sheet main body on a side of the cell storage containers and an expiration sheet having a ventilation property on a side opposite to the side of the cell storage containers. It is preferable that the flexible material sheet main body has holes for ventilating the inside and outside of the plurality of the cell storage containers.

The thickness of the flexible material sheet or the flexible material sheet main body is not particularly limited, but the lower limit of the thickness is more preferably 1 mm or greater and still more preferably 2 mm or greater from the viewpoint that the flexible material sheet or the flexible material sheet main body sufficiently follows the step and is not extremely thick. The upper limit of the thickness is not particularly limited, but is preferably 20 mm or less, more preferably 10 mm or less, and still more preferably 5 mm or less in a case of assuming the cost.

In a case where the flexible material sheet or the flexible material sheet main body has holes, it is preferable that the size thereof is determined based on the relationship between the size of the hole and the size of the opening portion of the cell culture insert described above. The size of the hole of the flexible material sheet or the flexible material sheet main body may be the size of a hole penetrating therethrough in a case of deformation, and the diameter of a hole assuming that the hole is a circle is preferably 0.5 mm or greater, more preferably 1 mm or greater, and still more preferably 2 mm or greater. The upper limit thereof is preferably 10 mm or less, more preferably 8 mm or less, and still more preferably 5 mm or less.

Figure 3:
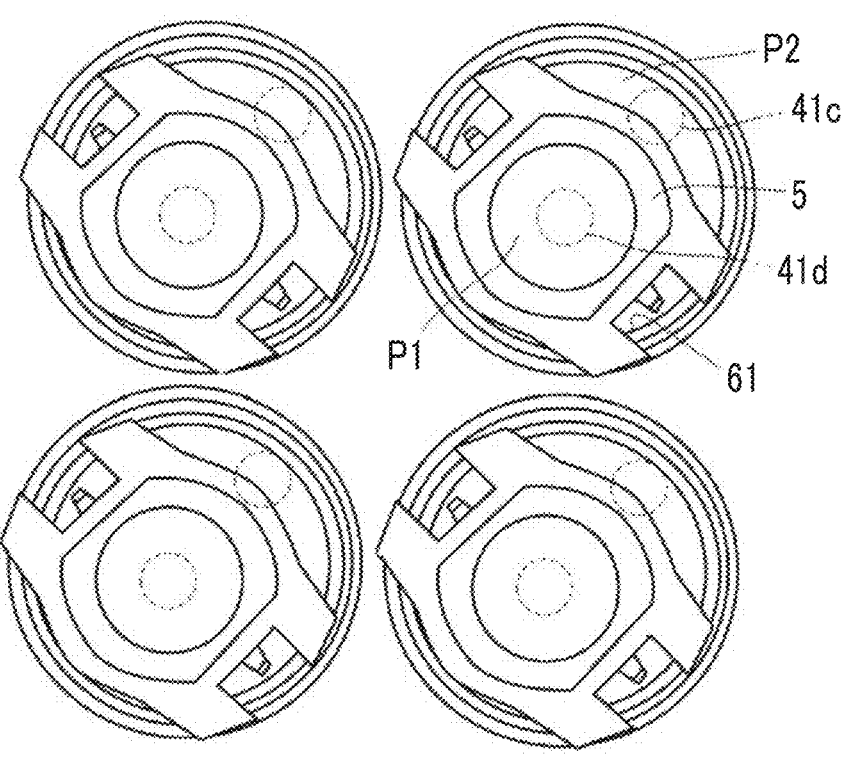
FIG. 3 is an enlarged plan view schematically illustrating a form of a hole 41 provided in a flexible material sheet main body 4.

The shape of the hole may be arbitrarily determined, but it is more practical that the hole has a circular shape. Alternatively, in a case where two holes are provided as illustrated in FIG. 3, the hole may have a gourd-like shape (a shape in which the central portion of an ellipse is constricted) in a front view in which the two holes are connected.

The thickness of the expiration sheet is not particularly limited, but the lower limit of the thickness is preferably 0.05 mm or greater, more preferably 0.1 mm or greater, and still more preferably 0.15 mm or greater. The upper limit of the thickness thereof is preferably 1 mm or less, more preferably 0.5 mm or less, and still more preferably 0.2 mm or less.

It is preferable that the expiration sheet has waterproofness. For example, in terms of the waterproofness, the water repellency is preferably 5 kPa or greater, more preferably 6 kPa or greater, still more preferably 7 kPa or greater, and particularly preferably 8 kPa or greater in conformity with JIS L 1092 (2009). The upper limit of the water repellency is not particularly limited, but is usually 50 kPa or less.

It is preferable that the expiration sheet has a ventilation property. In terms of the ventilation property, the Gurley air permeability is preferably 30 sec/100 $cm^3$ or less, more preferably 27 sec/100 $cm^3$ or less, still more preferably 25 sec/100 $cm^3$ or less, and particularly preferably 22 sec/100 $cm^3$ or less in conformity with TAPPI T460. The lower limit thereof is not particularly limited, but is usually 5 sec/100 $cm^3$ or greater.

Cells can be transported in a state where the influence on the cells is reduced by providing an expiration sheet having waterproofness and the ventilation property on the flexible material sheet or the flexible material sheet main body provided with holes. By employing the above-described configuration, a dedicated container for cell transportation as described in the documents of the related art is unnecessary, and sealing can be easily performed even in a case where the upper surface of the cell storage container is uneven.

It is preferable that the holes of the flexible material sheet main body are provided such that (1) at least one hole is provided inside the opening portion of the cell storage container and (2) at least one hole is provided outside the upper opening portion of the cell storage container and inside the upper opening portion of the recess of the plate by which the cell storage container is held. This point will be described in more detail in the explanation of FIG. 3 below.

It is also preferable that the holes of the flexible material sheet main body are provided to straddle between (1) the inside the opening portion of the cell storage container and (2) the outside the upper opening portion of the cell storage container and the inside the upper opening portion of the recess of the plate by which the cell storage container is held. This point will be described in more detail in the explanation of FIG. 4 below.

It is preferable that the flexible material sheet or the flexible material sheet main body is a gel sheet. The Asker C hardness of the flexible material sheet or the flexible material sheet main body in conformity with JIS K 7312 is preferably 40 degrees or less. The asker C hardness of the flexible material sheet or the flexible material sheet main body in conformity with JIS K 7312 is preferably 37 degrees or less, more preferably 35 degrees or less, and particularly preferably 32 degrees or less. The lower limit thereof is not particularly limited.

[Holding Member]

In a preferred embodiment of the cell preservation or transportation instrument of the present invention, the cell preservation or transportation instrument further includes a holding member for holding the plurality of cell storage containers, the plate, and the flexible material sheet in a state of compression in the thickness direction. A first example of the holding member is a holding member that includes a set of pressing plates and a plurality of bolts (see FIG. 1). Further, a second example of the holding member is a holding member that includes an outer storage container, an outer storage container upper lid, and a crimp locking unit crimping and locking the outer storage container and the outer storage container upper lid (see FIGS. 5, 6, and 7). As the holding member of the second example, for example, a commercially available iP-TEC® secondary container (G-28516, Sanplatec Co., Ltd.) can be used. In a case where the holding member of the second example is used, a gap is formed in the thickness direction depending on the shape of the outer storage container during storage of the plurality of cell storage containers, the plate, and the flexible material sheet in the outer storage container, and thus the plurality of cell storage containers, the plate, and the flexible material sheet may not be sufficiently compressed even in a case where the outer storage container upper lid and the outer storage container are crimped. In this case, the plurality of cell storage containers, the plate, and the flexible material sheet can be sufficiently compressed by disposing a spacer for adjusting the height at a lower part of the plate (see FIG. 8). The material and the shape of the spacer for adjusting the height are not particularly limited, and preferred examples thereof include a polycarbonate plate having an appropriate thickness.

[Cell Transportation Method]

A cell transportation method according to the embodiment of the present invention includes transporting the cell preservation or transportation instrument according to the embodiment of the present invention, in which cells are stored in at least some of the plurality of cell storage containers.

The type of cells used in the present invention is not particularly limited, and examples thereof include intestinal cells, hepatocytes, vascular endothelial cells, pancreatic beta cells, myocardial cells, nerve cells, cutaneous epithelial cells, cartilage cells, bone cells, tissue stem cells, ES cells (embryonic stem cells), and iPS cells (induced pluripotent stem cells).

The origins of cells such as intestinal cells, hepatocytes, vascular endothelial cells, pancreatic beta cells, myocardial cells, nerve cells, cutaneous epithelial cells, cartilage cells, and bone cells are not particularly limited, and cells collected from biotissues or cells obtained by being induced from stem cells may be employed. Further, the cells may be cells separated from biotissues (=first stage culture cells) or established cells.

In a case where cells are cultured using the cell preservation or transportation instrument according to the embodiment of the present invention before transportation of the cells, the cell culture temperature is preferably 4° C. or higher and 40° C. or lower, more preferably 10° C. or higher and 40° C. or lower, and particularly preferably 20° C. or higher and 40° C. or lower. It is preferable that air (particularly oxygen) and carbon dioxide are appropriately supplied to cells in order to culture the cells.

The cells can be stored in the cell storage container together with the cell culture medium as necessary during transportation of the cells.

The cell culture medium can be appropriately selected depending on the type of cells to be transported, and examples thereof include Dulvecco Modified Eagle Medium (DMEM), F12 culture medium, RPMI culture medium (GIBCO (registered trademark) RPMI1640 culture medium or the like), and a mixed culture medium of these, but the present invention is not particularly limited thereto. Serum, antibiotics, and the like can also be further added to the cell culture medium.

The temperature during transportation of the cells is not particularly limited, and the cells may be transported at room temperature or at a temperature adjusted to be in a range of 10° C. to 40° C. (preferably in a range of 20° C. to 40° C. and more preferably in a range of 30° C. to 40° C.). Alternatively, the cells may be transported in a refrigerated state (0° C. to 4° C.).

The transportation time is not particularly limited, and the lower limit thereof may be 1 hour or longer, 2 hours or longer, 3 hours or longer, 6 hours or longer, 12 hours or longer, 24 hours or longer, or 48 hours or longer, and the upper limit thereof may be 2 weeks or shorter or 1 week or shorter.

Preferred Embodiment

Hereinafter, the cell preservation or transportation instrument according to the preferred embodiment of the present invention will be described in more detail with reference to the accompanying drawings.

FIG. 1 is a developed perspective view schematically illustrating an embodiment of the cell preservation or transportation instrument of the present invention. An instrument 10 according to the present embodiment includes a pressing plate (upper) 1, a well plate lid 2, an expiration sheet 3, a flexible material sheet main body (gel sheet) 4, cell storage containers (cell culture inserts) 5, a well plate main body 6, a pressing plate (lower) 7, and screws (bolts) 19.

Figure 2:
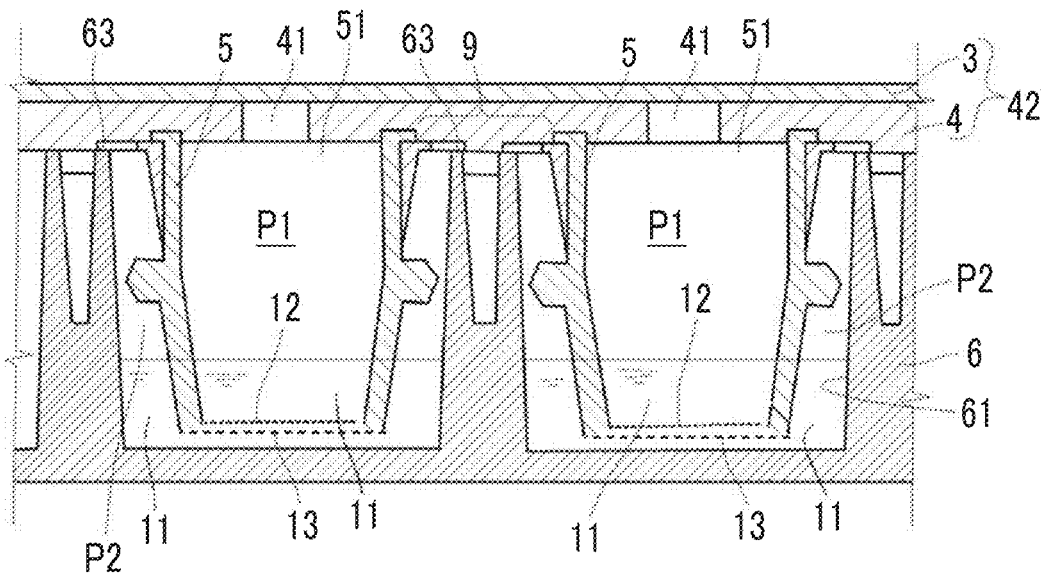
FIG. 2 is an enlarged partial cross-sectional view schematically illustrating the relationship between storage containers (cell culture inserts) and recesses (wells) of a well plate.

In a case of use, the storage containers 5 are inserted and arranged in wells (recesses) 61 of the well plate main body. Here, the culture medium is put into the recesses 61. The bottom portion of each cell culture insert 5 has a structure (for example, a mesh structure formed of a resin film) that allows the culture medium to permeate. Therefore, in a case where the cell culture inserts 5 are placed in the wells 61, the culture medium flows from the wells 61 (external regions P2) into internal regions P1 of the cell culture inserts 5 (FIG. 2).

Next, the gel sheet 4 is disposed on the cell culture inserts 5 so as to cover the cell culture inserts 5. The expiration sheet 3 is disposed on the gel sheet 4. In the present specification, a combination of the gel sheet (flexible material sheet main body) 4 and the expiration sheet 3 is referred to as a flexible material sheet 42.

The flexible material sheet has a shape in which the expiration sheet 3 and the gel sheet 4 are bonded to each other in advance, and the cell culture inserts 5 may be covered with the expiration sheet 3 and the gel sheet 4.

Next, the well plate lid 2 is used to cover the sheets so that the well plate lid 2 comes into contact with the well plate main body 6 and the inside of the containers is sealed.

Further, in the present embodiment, the pressing plate (upper) 1 and the pressing plate (lower) 7 are prepared, and these pressing plates are screwed and fixed with the bolts 19. In this manner, the gel sheet 4 is firmly attached to the cell culture inserts 5, and the well plate lid 2 is unexpectedly opened to prevent the contents from spilling out.

FIG. 2 is a partial cross-sectional view schematically illustrating the relationship between the storage containers (cell culture inserts) 5 and the wells (recesses) 61 of the well plate. A bottom portion 13 of each cell culture insert 5 has a mesh structure through which the culture medium 11 can permeate as described above. The bottom portion 13 having such a mesh structure can be formed of a resin film such as polyethylene terephthalate. FIG. 2 illustrates a form in which cells 12 are fixed on the bottom portion 13 of the cell culture insert. The culture medium in an amount sufficient for covering the cells 12 is supplied to the inside of the cell culture insert 5. As described above, the well 61 is filled with a sufficient amount of the culture medium 11. By inserting the cell culture insert 5 into the well 61, the culture medium also comes into contact with the mesh side of the bottom portion 13, and thus the state of liquid phase culture is realized.

As illustrated in FIG. 2, in the instrument of the present embodiment, the flexible material sheet main body 4 is disposed to seal an opening portion 51 at the upper part of the cell culture insert 5. For example, a gel sheet is used for the flexible material sheet main body. Therefore, the gel sheet has sufficient flexibility and is thus attached to a step 9 formed by the upper end portion of the cell culture insert and the upper end portion of the well side wall (upper side wall portion 63) of the well plate by suitably responding to and following the step 9. Further, since the gel sheet has appropriate adhesiveness, liquid leakage does not occur even in a case where the instrument is shaken, laid down, or turned upside down.

In the present embodiment, holes 41 are formed in the flexible material sheet main body 4. The ventilation property of the expiration sheet at the upper part is exhibited due to the presence of the holes. That is, gas (oxygen) that has permeated the expiration sheet 3 through the holes 41 is supplied to the inside of the cell culture inserts. A healthy state of the cells is maintained by supplying the gas (oxygen) to the cells 12 through the culture medium.

The form of the holes 41 formed in the flexible material sheet 4 is not particularly limited, but it is preferable that each hole is formed at least in a region of the opening portion 51 of the cell culture insert. In this manner, the function of maintaining cells is exhibited due to the permeation of gas (particularly oxygen) through the expiration sheet 3.

Figure 4:
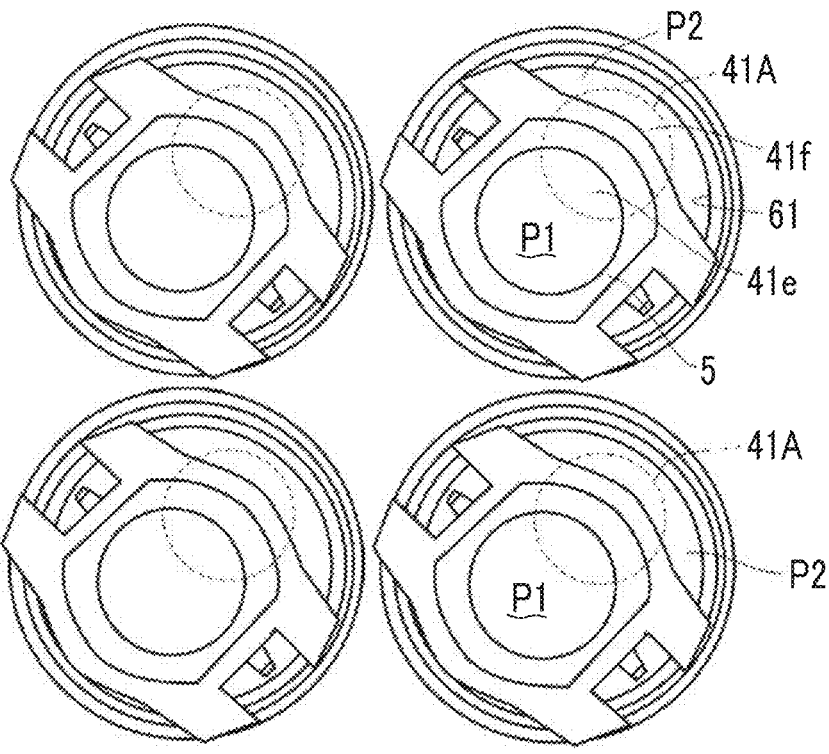
FIG. 4 is an enlarged plan view schematically showing another form of the hole 41 provided in the flexible material sheet main body 4.

FIGS. 3 and 4 are each an enlarged plan view schematically illustrating the form of the holes 41 provided in the flexible material sheet main body 4.

In the form illustrated in FIG. 3, a hole 41$d$ in an internal region P1 of the cell culture insert 5 (hereinafter, also referred to as an internal region) and a hole 41$c$ in a region P2 that is outside the cell culture insert and inside the well 61 of the well plate 6 (hereinafter, also referred to as an external region) are illustrated. In the figure, the positions of the holes are indicated by broken lines for convenience of illustration.

The balance between the internal pressure of the internal region P1 of the cell culture insert and the internal pressure of the external region P2 is ensured due to the action of the holes. The internal region P1 and the external region P2 of the cell culture insert are in a state where the culture medium (liquid) can be migrated through the film 13 having micropores provided at the bottom portion of the cell culture insert as described above. In a case where the gel sheet does not have holes, problems of an increase in the internal pressure of the internal region P1 of the cell culture insert, migration of the culture medium 11 from the internal region P1 of the cell culture insert to the external region P2, and exposure of the cells 12 occur, but such problems can be avoided by forming holes, which is preferable. There are several possible reasons for the increase in the internal pressure, and for example, the internal pressure is increased because the degree of attachment of the gel sheet 4 to the opening portion 51 of the cell culture insert is slightly stronger than the degree of attachment of the gel sheet 4 to the step 9, because the degree of sealing of the internal region P1 of the cell culture insert is stronger than the degree of sealing of the external region P2, or because the internal pressure of the internal region P1 where the degree of sealing is slightly stronger is greater than the internal pressure of the external region P2 in a case where the transportation instrument is heated to a temperature (around 35° C.) suitable for the cell.

In the form illustrated in FIG. 4, a relatively large hole 41A is provided. By providing the hole 41A to be relatively large, a portion 41e overlapping the internal region P1 of the cell culture insert and a portion 41f overlapping the region (external region) P2 outside the internal region are generated, and thus occurrence of a difference in the internal pressure between two regions can be prevented.

Figure 5:
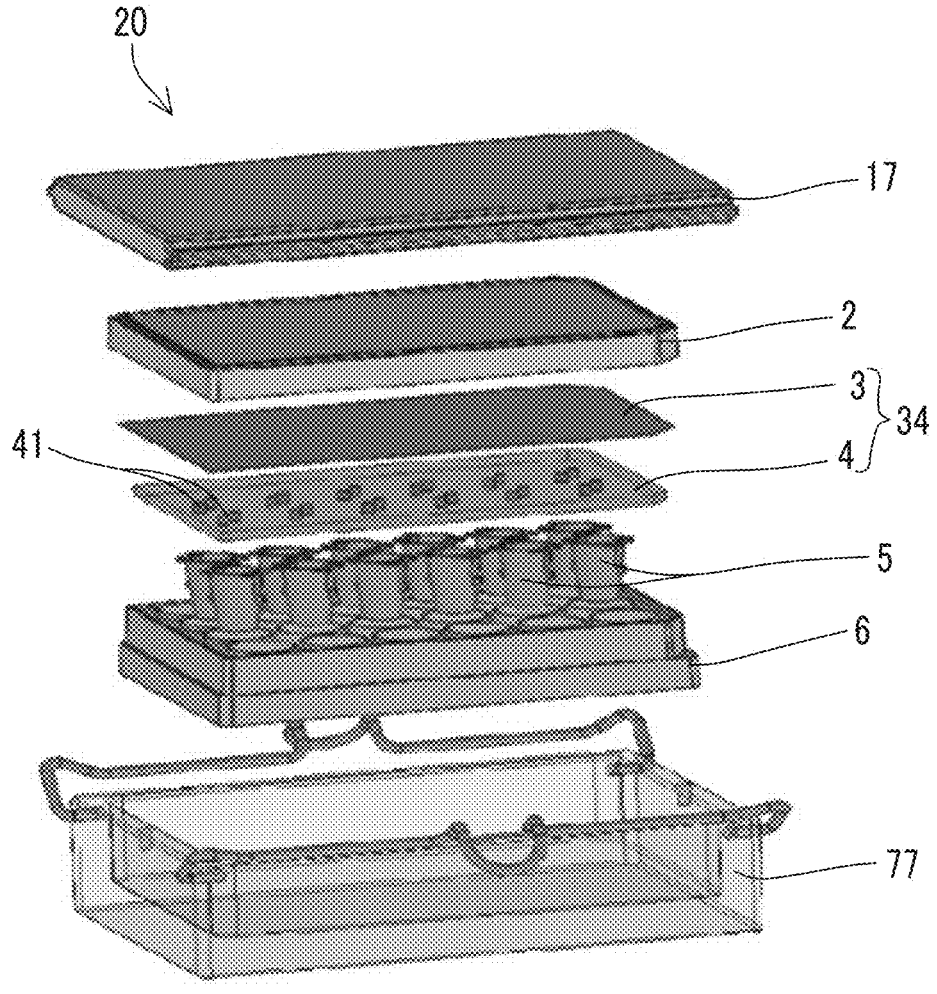
FIG. 5 is a developed perspective view schematically illustrating another embodiment of the cell preservation or transportation instrument of the present invention.
Figure 6:
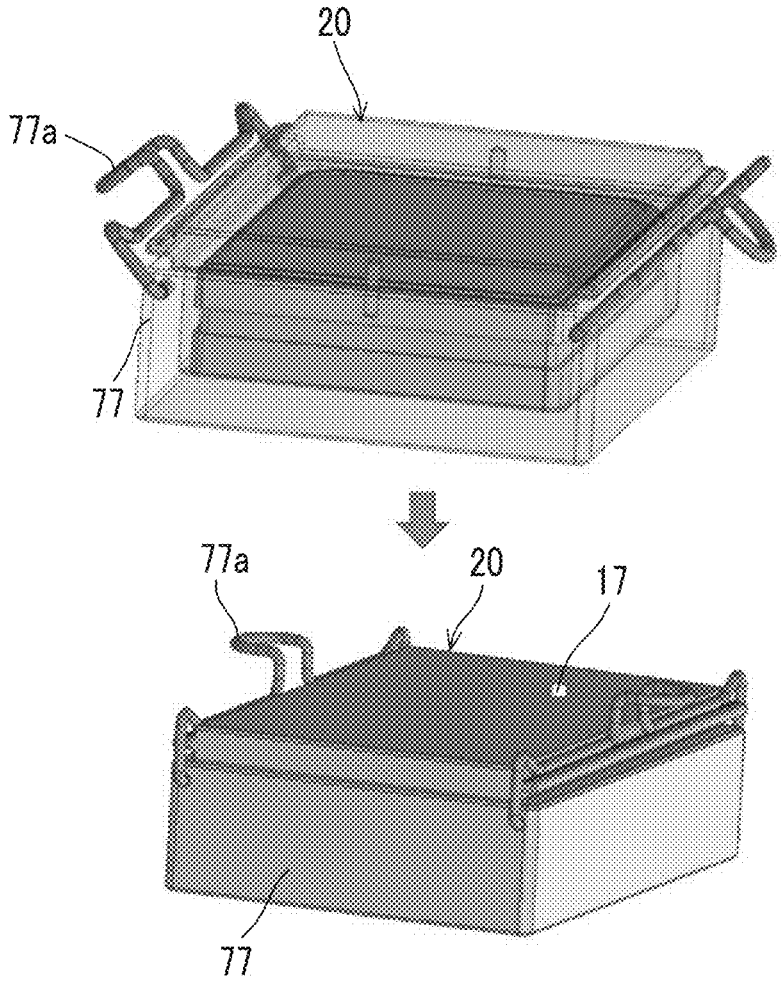
FIG. 6 is a perspective view schematically illustrating a closed form of the instrument illustrated in FIG. 5.
Figure 7:
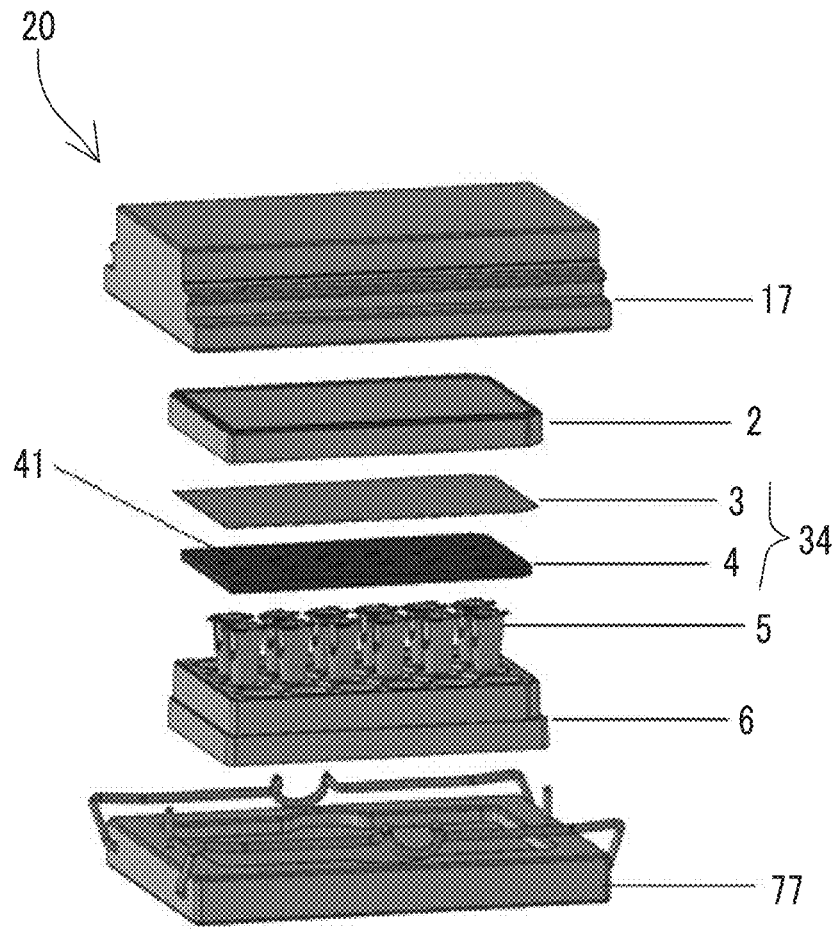
FIG. 7 is a developed perspective view schematically illustrating still another embodiment of the cell preservation or transportation instrument of the present invention.

FIG. 5 is a developed perspective view schematically illustrating another embodiment of the cell preservation or transportation instrument of the present invention. An instrument 20 of the present embodiment is different from the instrument illustrated in FIG. 1 in terms that an outer storage container upper lid 17 which is a dedicated pressing plate and an outer storage container 77 with a crimp locking tool are employed. By employing such a configuration, the instrument can be easily fixed by simply reclining the crimp locking tool toward the upper lid. FIG. 6 is a perspective view illustrating the movement in a case of reclining the crimp locking tool 77a. According to the instrument of the present embodiment, the instrument can be easily fixed without troublesome screwing work. FIG. 7 is a developed perspective view schematically illustrating still another embodiment of the cell preservation or transportation instrument of the present invention. Since the depth of the storage portion of the well plate main body 6 of the outer storage container 77 with a crimp locking tool is less than that of FIG. 5, the well plate main body 6 can be more easily taken out from the outer storage container. A rod at the right end of the outer storage container 77 with a crimp locking tool indicates a positioning pin.

Figure 8:
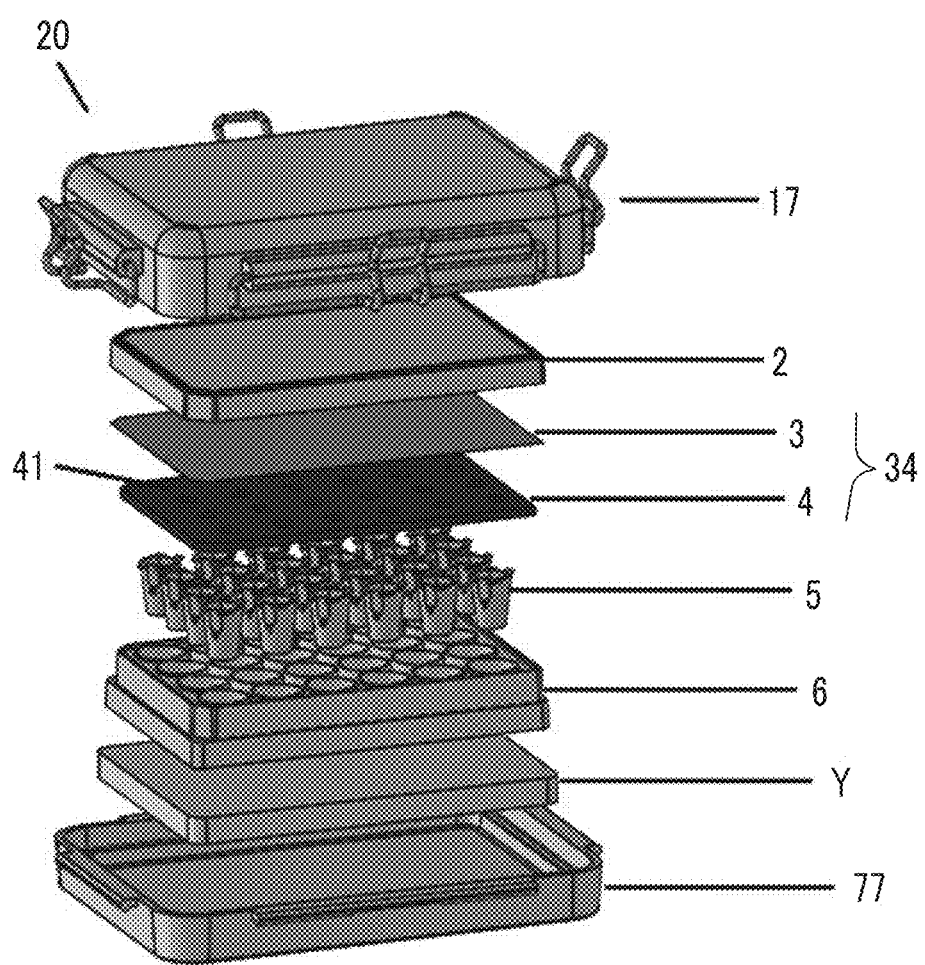
FIG. 8 is a developed perspective view schematically illustrating even still another embodiment of the cell preservation or transportation instrument of the present invention.

FIG. 8 is a developed perspective view schematically illustrating still another embodiment of the cell preservation or transportation instrument of the present invention. As the outer storage container 77 with a crimp locking tool, a commercially available iP-TEC® secondary container is used. A spacer Y for adjusting the height is provided at the lower part of the well plate main body 6. By employing such a configuration, the cell storage container, the plate, and the flexible material sheet can be sufficiently compressed by the outer storage container 77 with a crimp locking tool regardless of the dimensions of the outer storage container 77 with a crimp locking tool in the thickness direction.

<Cell Culture Insert (Cell Storage Container)>

The cell preservation or transportation instrument according to the embodiment of the present invention has a plurality of cell storage containers (also referred to as cell culture inserts). It is preferable that a PET film having micropores with a size of several micrometers is provided on the bottom surfaces of the cells of the cell culture insert such that the cells can be cultured on the film. Specifically, as the cell culture insert, a falcon (registered trademark) (manufactured by Corning Inc.) cell culture insert or the like can be used.

<Well Plate>

It is preferable that the well plate stores the cell culture insert in each well and can suitably hold the culture medium for culturing cells in the well. Specifically, a falcon (registered trademark) (manufactured by Corning Inc.) 24-well plate or the like can be used.

<Gel Sheet (Flexible Material Sheet Main Body)>

Specific examples of the gel sheet include a resin sheet such as polyurethane or silicone. Specifically, suitable examples thereof include Hypergel t3 (EXSEAL Corporation, t1 Asker C hardness of 30), human skin gel (urethane-based) (EXSEAL Corporation, t3 hardness of 0), and Lambda gel (silicone-based) (Taica Corporation).

It is preferable that the gel sheet constituting the flexible material sheet main body has a low hardness, which is a characteristic of the material, and exhibits high sealability by following the step at the upper end of the side wall of the well plate. For example, it is preferable that the sealability enables the culture medium inside the container to be held even in a case of liquid shake due to vibration during transportation.

The gel sheet provided with expiration holes through which oxygen required for cells can be supplied to the cells is desirable.

A first specific example of the holes provided in the gel sheet (flexible material sheet main body) is a form in which (1) at least one hole is provided in the opening portion of the cell storage container and (2) at least one hole is provided outside the upper opening portion of the cell storage container and inside the upper opening portion of the recess of the plate by which the cell storage container is held (FIG. 3). Alternatively, a second specific example thereof is a form in which holes are provided to straddle between (1) the inside the opening portion of the cell storage container and (2) the outside the upper opening portion of the cell storage container and the inside the upper opening portion of the recess of the plate by which the cell storage container is held (FIG. 4).

<Expiration Sheet (Ventilation Sheet)>

Examples of the expiration sheet include an expiration sheet of Tyvek (registered trademark) 1073B (manufactured by DuPont). It is preferable that the expiration sheet has waterproofness and the ventilation property to prevent the culture medium from coming out through the holes provided in the flexible material sheet main body. Examples of such an expiration sheet include PET-based non-woven fabric.

<Pressing Plate (Holding Member) (Upper and Lower)>

As an example, upper and lower pressing plates (holding members) and bolts are employed in order to appropriately press the gel sheet. Examples of the pressing plate include a polycarbonate plate t10. Further, a combination of the polycarbonate plate t10 and bolts may be used.

The thickness of the pressing plate is not particularly limited, but the lower limit of the thickness is preferably 5 mm or greater, and the upper limit thereof is preferably 20 mm or less.

As a modified example of the preservation or transportation instrument according to the embodiment of the present invention, an instrument that has employed a gel sheet with satisfactory gas permeability is exemplified. In this manner, formation of the expiration sheet or holes can be omitted. The oxygen concentrations of the materials exemplified above after a predetermined time (1 hour) after degassing oxygen are listed for reference (see FIG. 10). In this manner, the instrument can be configured without employing the expiration sheet. The dimensions in FIG. 10 denote the thicknesses of the gel sheets.

Figure 10:
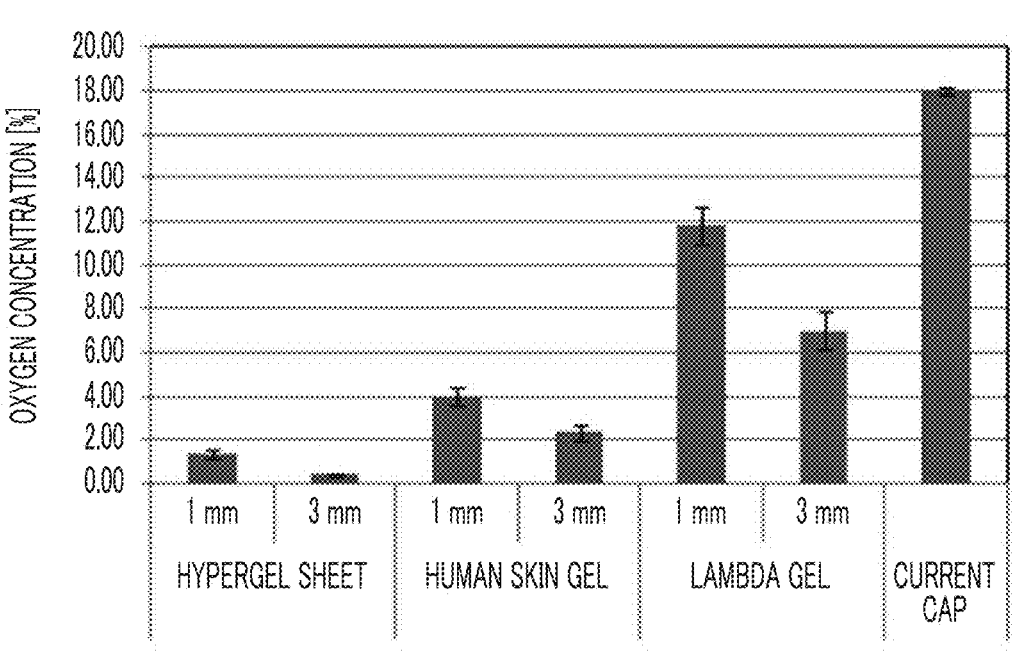
FIG. 10 is a graph comparing the oxygen permeabilities of various gel sheets.

In FIG. 10, the hypergel sheet denotes "Hypergel t3 (EXSEAL Corporation, t1 Asker C hardness of 30)", the human skin gel denotes "human skin gel (urethane-based) (EXSEAL Corporation, t3 hardness of 0)", the lambda gel denotes "Lambda gel (silicone-based) (Taica Corporation)", and the current cap denotes "iP-TEC dish cover (Sanplatec Co., Ltd., cap made of a silicone material with a thickness of 0.5 mm at a predetermined site).

The measuring method of FIG. 10 is as follows. One side separated by a gel sheet, which is an object to be measured, is degassed to create a vacuum (oxygen-free side), the other side is in contact with the atmosphere (atmosphere side), and the amount of oxygen to permeate from the atmosphere side to the oxygen-free side through the gel sheet after 1 hour is measured using an oxygen concentration meter (MODEL 3600 type, Hach Ultra Analytics Inc.) installed on the oxygen-free side.

Alternatively, gas may be allowed to permeate therethrough by making a predetermined site thin instead of forming holes in the gel sheet. Even in this embodiment, the number of members can be reduced without employing the expiration sheet.

According to the preferred embodiment of the present invention, sealing can be performed by placing the flexible material sheet main body (for example, a gel sheet (with a hardness of 40 degrees or less and preferably 30 degrees or less in terms of Asker C hardness) on the opening portion so as to cover the unevenness of the opening portion using the well plate used for culturing cells and the cell culture insert as they are, and familiarizing the flexible material sheet main body with the unevenness. The migration of the culture medium into and out of cells of the culture medium through the film applied to the cells caused by an increase in internal pressure due to an increase in the temperature to the temperature (usually 37° C.) in a state of supply oxygen to the cells during transportation is suppressed. Therefore, it is preferable to provide at least one hole in the flexible material sheet main body so as to overlap with at least the inside of the cell culture insert. The diameter of the hole is approximately in a range of 1 to 8 mm as described above, but is not particularly limited. Further, it is preferable that the transportation is carried out by covering the well plate with a lid in a state where a film (for example, Tyvek (registered trademark) 1073B) with excellent waterproofness and an excellent ventilation property is provided on the upper part of the gel sheet in order to prevent liquid leakage from the hole and sandwiching the uneven container with a force of following the uneven container without destroying the gel sheet.

As a method of sandwiching the uneven container, the uneven container may be sandwiched by a plate and bolts (see FIG. 1) or may be stored in a container with a pressable lid such as a lunch box with a crimp locking tool (packing) (see FIGS. 5 and 6).

The present invention will be described in more detail with reference to the following examples, but the present invention is not limited to the examples.

EXAMPLES

[Preparation of Sample]

Cells were preserved and transported using the instrument illustrated in FIG. 1. The materials employed here are described below.

<Well Plate>

Falcon (registered trademark) 24-well plate (with 4 rows×6 columns of wells) (Corning Inc.)

<Cell Culture Insert>

Falcon (registered trademark) cell culture insert (Corning Inc.)

A PET film in which micropores having a diameter of several micrometers was attached to the bottom surface of the cell culture insert. Cells were cultured on the PET film.

<Gel Sheet>

Hypergel (EXSEAL Corporation), Asker hardness of 30 (type C), thickness of 3 mm

Holes through which oxygen required for cells was able to be supplied were formed in the form required for the following individual tests.

<Expiration Sheet>

Tyvek (registered trademark) 1073B (DuPont)

Water repellency (JIS L 1092) of 8 kPa or greater

Thickness of approximately 0.18 mm

Ventilation property: Gurley air permeability (TAPPI T460) of 22 sec/100 cc

PET-based non-woven fabric having waterproofness and the ventilation property was used.

<Pressing Plate and the Like>

Polycarbonate plate t10 (thickness of 10 mm) and bolts

<Used Cells>

Intestinal epithelium differentiation-induced by the method described in the pamphlet of WO2019/156200A <Conditions for Culturing Cells>

Culture medium: culture medium in a case of intestinal epithelium cells being differentiation-induced by the method described in the pamphlet of WO2019/156200A Additive culture medium amount: inside cell culture insert—150 μL/outside cell culture insert—600 μL Seeding density: $6.6 \times 10^4$ cells/well Example 1: Confirmation 1 of Liquid Leakage Water colored with red food coloring was poured into the well of the instrument of FIG. 1 described above. Holes having a diameter of 3 mm were provided in the gel sheet of the instrument at positions corresponding to 41c and 41d of FIG. 3. The instrument was turned upside down and allowed to stand for 3 hours. As a result, liquid leakage did not practically occur. Only slight bleeding occurred and the problem of liquid leakage did not occur.

Example 2: Confirmation 2 of Liquid Leakage

Water colored with red food coloring was poured into the well of the instrument of FIG. 1 described above. Holes having a diameter of 3 mm were provided in the gel sheet of the instrument at positions corresponding to 41c and 41d of FIG. 3. An instrument containing colored water was set on a mixer (TRIO HM-IN: As One Corporation, amplitude of 4.5 mm) and vibrated for 1 hour to confirm whether the colored water in the well leaked. The vibration condition at this time was set to a condition that the amplitude was the widest visually. As a result, no liquid leakage occurred.

Example 3: Confirmation of Oxygen Permeation

A temporal change in the oxygen concentration was measured by a measuring device (Fibox4, PreSens Precision Sensing GmbH). The oxygen concentration was measured by attaching a sensor to the bottom of the well plate.

The measurement was started after water was poured into the wells of the instrument of FIG. 1 described above, nitrogen was blown into the wells, and the oxygen concentration was set to 5% or less.

Figure 11:
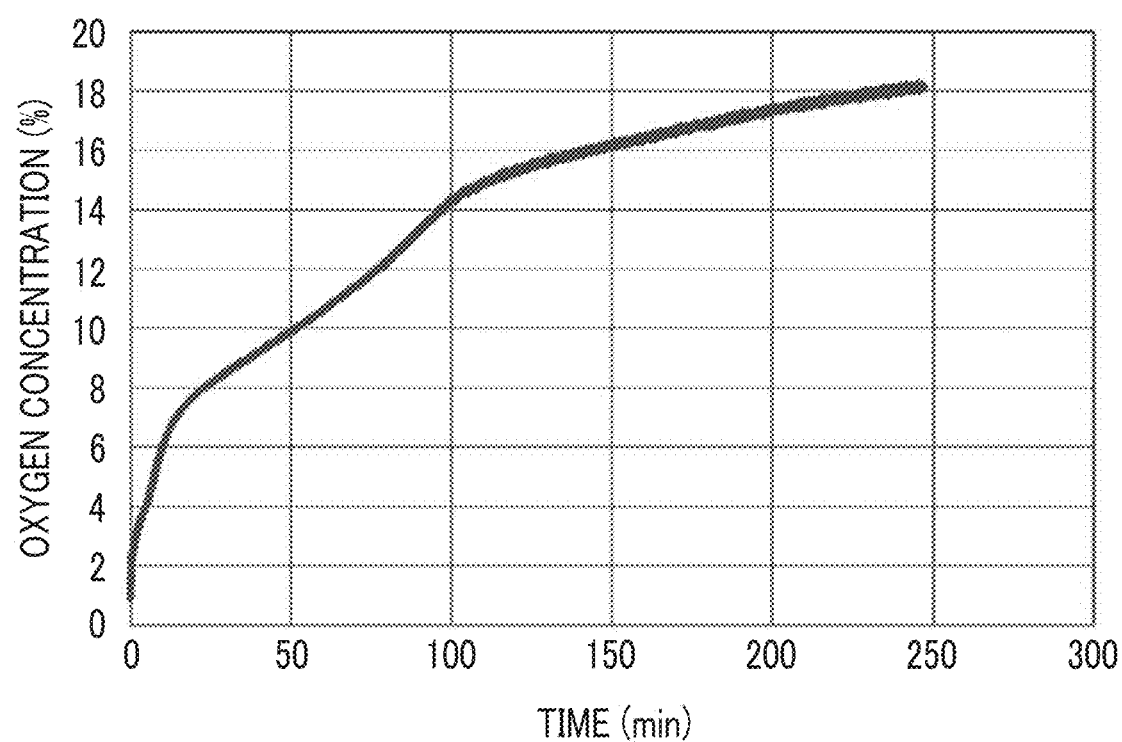
FIG. 11 is a graph showing a temporal change in the oxygen concentration in a storage container in a state where only the well plate is covered with a lid without covering an opening portion of the storage container.

In a case where the oxygen concentration was measured in a state where only a lid was placed on the well plate, the oxygen concentration was recovered to 18% in approximately 4 hours (see FIG. 11).

Figure 12:
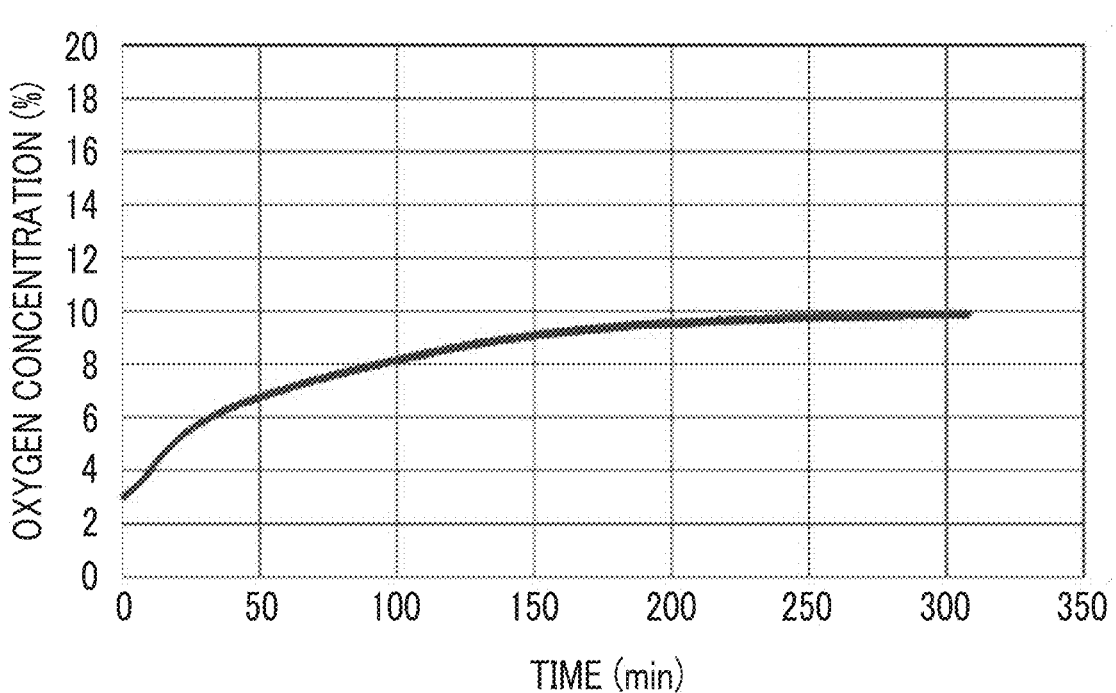
FIG. 12 is a graph showing a temporal change in the oxygen concentration in a storage container in a state where the opening portion of the storage container is sealed with a flexible material sheet (having no holes).

In a case where a gel sheet (without holes) was provided, the oxygen concentration was recovered only to 10% in approximately 4 hours (see FIG. 12).

Figure 13:
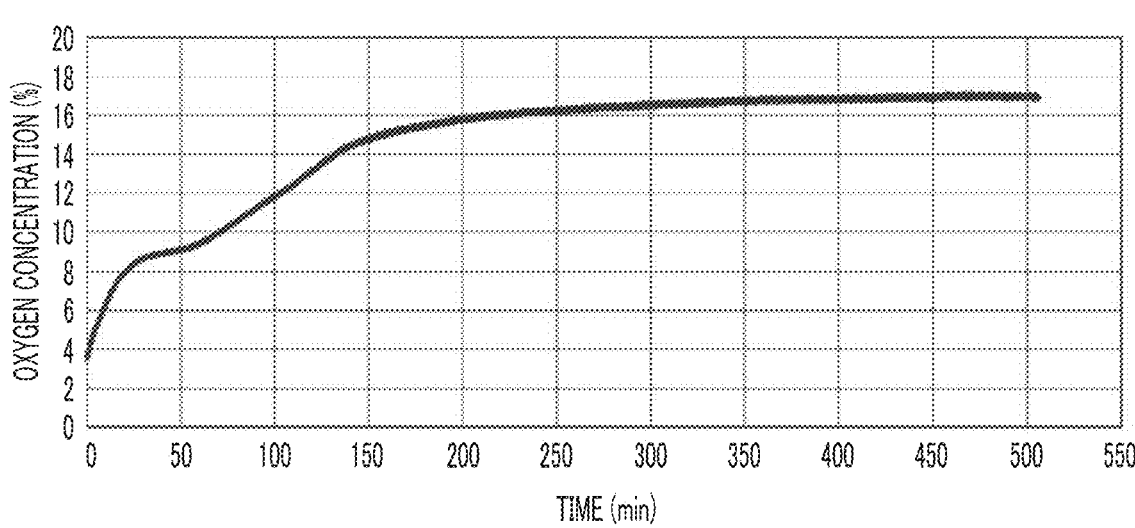
FIG. 13 is a graph showing a temporal change in the oxygen concentration in a storage container in a state where the opening portion of the storage container is sealed with a flexible material sheet (having holes).

In a case where a gel sheet (with holes) was provided, the oxygen concentration increased slightly slower than the case where the well plate was covered only by a lid, and as a result, the oxygen concentration that finally reached was also low, but the oxygen concentration was recovered to approximately 17% in approximately 4 to 5 hours (see FIG. 13). Therefore, it was found that oxygen was sufficiently permeable as compared with the case where the gel sheet without holes was provided. Here, the holes have a diameter of 6 mm and were formed as the hole 41A in FIG. 4.

Example 4: Change in Transepithelial Electrical Resistance (TEER) of Cells Depending on Size and Number of Holes The transepithelial electrical resistance (TEER) was measured using a sample in the preservation and transportation form of cells using the instrument illustrated in FIG. 1. That is, the TEER of the cells before being cultured in the preservation and transportation form and the TEER of the cells after being cultured in the preservation and transportation form for 24 hours were measured, and the change was measured. The cells and the culture conditions were as described in the section of [Preparation of sample], and the culture temperature was 37° C. The influence of the gel sheets was investigated by forming different numbers of holes with difference sizes in the gel sheets used for the preservation and transportation form. The measuring device and the measuring method for TEER are as follows.

\<TEER Measuring Device\>

EVOM2 (manufactured by WPI)

ENDOHM-6 (manufactured by WPI)

CABLAY, ENDOHM-24 & 96 (manufactured by WPI)

\<TEER Measuring Method\>

(1) Cell culture inserts were set in ENDOHM-6 to which 500 μL of the culture medium had been added.

(2) The values displayed on EVOM2 were transcribed (blank inserts containing no cells were measured in the same manner as described above).

(3) The TEER values were calculated ((value in (2))– (value of blank insert in (2))×area (0.33 cm$^2$).

Figure 14:
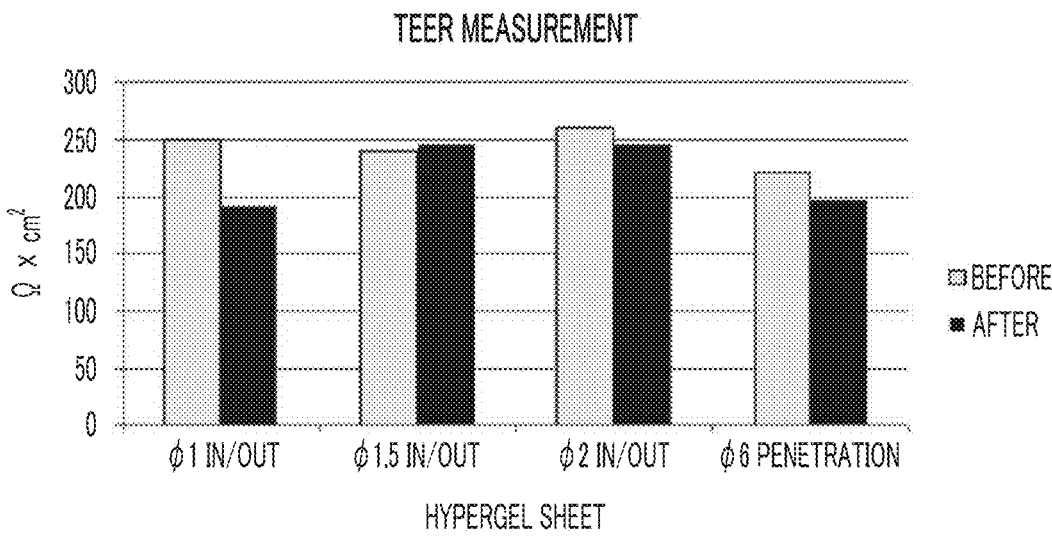
FIG. 14 is a bar graph comparing before and after incubation of transepithelial electrical resistance (TEER) due to holes and sterilization.

The measurement results are shown in FIG. 14.

The abbreviations in FIG. 14 have the following meanings. "φ1 in/out" denotes that holes having a diameter of 1 mm were provided at positions corresponding to the inside and the outside (P1, P2) of the cell culture insert. "φ1.5 in/out" denotes that holes having a diameter of 1.5 mm were provided at positions corresponding to the inside and the outside (P1, P2) of the cell culture insert. "φ2 in/out" denotes that holes having a diameter of 2 mm were provided at positions corresponding to the inside and the outside (P1, P2) of the cell culture insert. "φ6 penetration" denotes that holes having a diameter of 6 mm were provided to straddle the inside and the outside (P1, P2) of the cell culture insert.

As shown in the results of FIG. 14, it was found that holes are preferably formed in the gel sheet in order to suppress an increase in the internal pressure of the cell culture insert and to satisfactorily culture the cells.

Example 5: Confirmation of Liquid Migration in Cells

The test was performed using the instrument of FIG. 1 described above. The gel sheets of the transportation instrument were prepared depending on the following four types of cases.

(1) A case where holes were not formed.

(2) A case where holes having a diameter of 1 mm were provided at positions corresponding to the inside and the outside (P1, P2) of the cell culture insert (form of FIG. 3).

(3) A case where holes with a diameter of 1 mm were provided at positions corresponding to the inside (P1) of the cell culture insert.

(4) A case where holes having a diameter of 6 mm were provided to straddle the inside and the outside (P1, P2) of the cell culture insert (form of FIG. 4).

In the case (1), colored water colored with red food coloring was poured into three sites of the well plate such that 200 μL of colored water was added to the inside of the cell culture insert and 600 μL of colored water was added to the outside of the cell culture insert, the time was allowed to elapse in an incubator at 37° C. for 24 hours. Colored water colored with red food coloring was poured into six sites of the well plate in the cases (2) and (3) and colored water was poured into twelve sites of the well plate in the case (4) such that 200 μL of colored water was added to the inside of the cell culture insert and 600 μL of colored water was added to the outside of the cell culture insert, and transportation was carried out using heat retaining boxes to which heat storage materials had been respectively added (approximately 1 day elapsed). The amount of liquid in the wells after time elapse was observed.

In the case (1), the liquid was not found in the cell (P1) at three sites of the well plate (the liquid was migrated to the outside).

Figure 15:
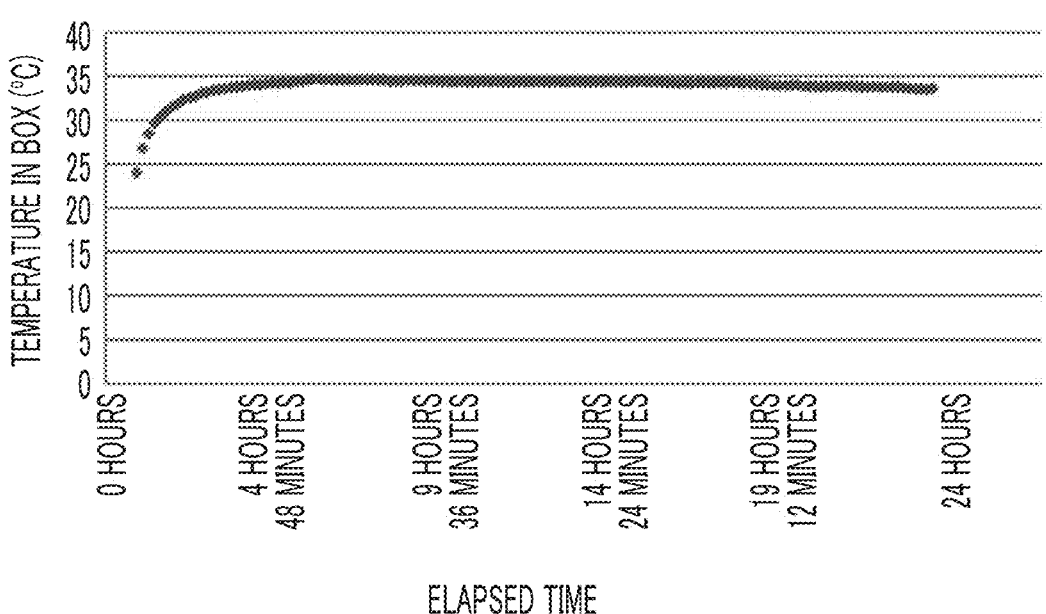
FIG. 15 is a graph showing a temporal change in the temperature in a storage container during transportation of the cell preservation or transportation instrument.

In the cases (2), (3), and (4), liquid migration was not observed in all the cells. Further, FIG. 15 shows the results obtained by measuring the internal temperature during transportation using the heat retaining box.

Example 6: Evaluation by Actual Transportation

The cells were transported by a general transporter using the instrument of FIG. 1 described above and the instrument in the preservation and transportation form of FIG. 3 or 4. The cells and the culture conditions were as described in the section of [Preparation of sample], and the transportation was carried out in the same manner as in Example 5 using heat retaining boxes to which heat storage materials had been respectively added (approximately 1 day elapsed). The TEER (transepithelial electrical resistance) was measured by the following devices and procedures before and after the transportation.

\<TEER Measuring Device\>

EVOM2 (manufactured by WPI)

ENDOHM-6 (manufactured by WPI)

CABLAY, ENDOHM-24 & 96 (manufactured by WPI)

\<TEER Measuring Method\>

(1) Cell culture inserts were set in ENDOHM-6 to which 500 μL of the culture medium had been added.

(2) The values displayed on EVOM2 were transcribed (blank inserts containing no cells were measured in the same manner as described above).

(3) The TEER values were calculated ((value in (2))– (value of blank insert in (2))×area (0.33 cm²).

Figure 16:
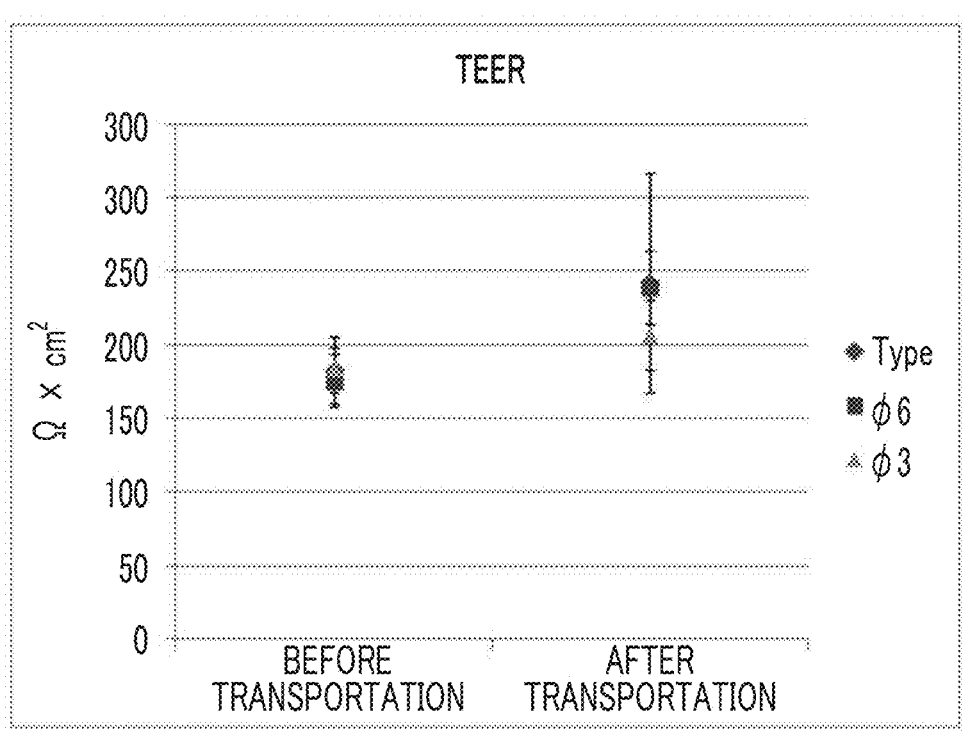
FIG. 16 is a graph showing TEER before and after transportation of the cell preservation or transportation instrument.

The measurement results of TEER are shown in FIG. 16. In the figure, "φ6" denotes that holes having a diameter of 6 mm were provided in the gel sheet. The holes were disposed as the hole 41A of FIG. 4. "φ3" denotes that holes having a diameter of 3 mm were provided in the gel sheet. The holes were disposed as the holes 41*c* and 41*d* of FIG. 3. "Type" denotes the result obtained by culturing and preserving the cells at 37° C. and 5% $CO_2$.

The TEER value after transportation is approximately the same as the value before transportation. It was found that the instruments had sufficient stability in practical use.

Example 7: Evaluation (2) by Actual Transportation

Figure 9:
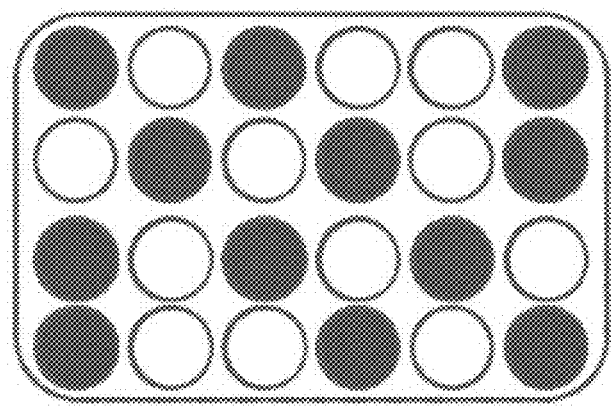
FIG. 9 illustrates arrangement of cell culture inserts.

The cells were transported by a general transporter using the instrument of FIG. 5 described above and the instrument in the preservation and transportation form of FIG. 4. The cells and the culture conditions are as described in the section of [Preparation of sample]. Here, 24 cell culture inserts were stored in the well plate. Among these, the cells were cultured in 12 cell culture inserts and the cells were not cultured in the remaining 12 cell culture inserts. The arrangement of the cell culture inserts is as shown in FIG. 9 (in FIG. 9, the filled circles indicate the cell culture inserts in which the cells were cultured, and the white circles indicate the cell culture inserts in which the cells were not cultured). Further, the transportation was carried out in the same manner as in Example 5 using heat retaining boxes to which heat storage materials had been respectively added (approximately 1 day elapsed). Leakage of the culture medium accompanied by the transportation and dislocation of the cell culture inserts did not occur. TEER was measured before and after transportation and after recovery culture one day after transportation, and CYP3A4 activity and gene expression of the small intestine marker and the liver marker were respectively measured after transportation.

Figure 17:
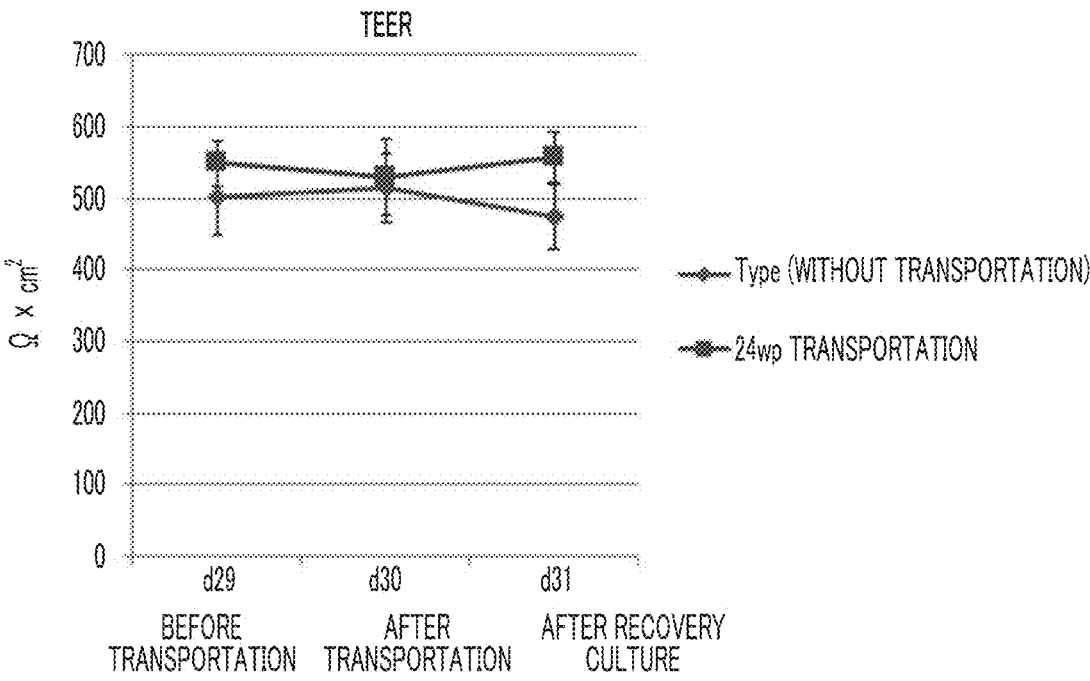
FIG. 17 is a graph showing TEER before transportation and after transportation of the cell preservation or transportation instrument, and after recovery culture.

The TEER was measured by the same devices and procedures as in Example 6. The results are shown in FIG. 17. "Type" denotes the result obtained by culturing and preserving the cells at 37° C. and 5% $CO_2$.

The TEER value after transportation is approximately the same as the value before transportation and the value obtained by culturing the cells without transportation. It was found that the instruments had sufficient stability in practical use.

Figure 18:
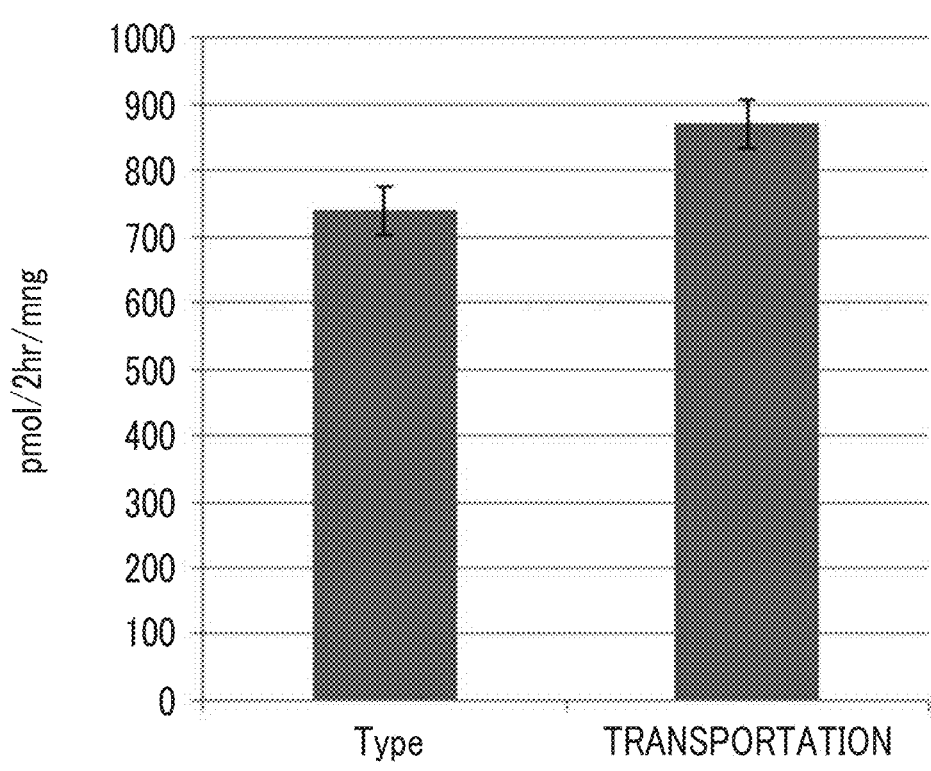
FIG. 18 shows the results of measuring CYP3A4 activity for cells cultured without transportation and cells after transportation.

The CYP3A4 activity was measured from the amount of midazolam metabolites. After transportation, intestinal epithelial cells were incubated with a culture medium containing 5 μmol/L of midazolam at 37° C., and the medium was sampled after 2 hours. Metabolic activity was calculated from the amount of 1-hydroxide midazolam in the culture medium measured using a liquid chromatography-mass spectrometer (LC-MS/MS). After completion of the metabolism experiment, protein was quantified and the metabolic activity was corrected by the amount of protein. The results are shown in FIG. 18. "Type" denotes the result obtained by culturing and preserving the cells at 37° C. and 5% $CO_2$.

The CYP3A4 activity after transportation shows approximately the same value as the value obtained by culturing the cells without transportation. It was found that the instruments had sufficient stability in practical use.

Gene expression was measured by extracting RNA from intestinal epithelial cells after transportation using RNeasy (registered trademark) Mini Kit (Qiagen). The operation was performed according to the attached manual. As a reverse transcription reaction, the synthesis of complementary DNA (cDNA) was carried out using High capacity RNA-to-cDNA Kit (applied biosystems). The operation was performed according to the attached manual.

The real-time reverse transcription polymerase chain reaction (Real-Time RT-PCR) was carried out using TaqMan (registered trademark) Gene Expression Master Mix (applied biosystems) and using cDNA as a template. The operation was performed according to the manual. The measurement results were corrected using 18S ribosome as an endogenous control. The expression level of mRNA was estimated using probes of various genes. The results are listed in Table 1. The numerical values in Table 1 denote the relative expression levels in a case where the expression level in Adult Institute was set to 100 for the small intestine marker and denote the relative expression levels in a case where the expression level in Caco-2 was set to 100 for the liver marker. "Type" denotes the result obtained by culturing and preserving the cells at 37° C. and 5% $CO_2$.

The gene expression after transportation shows approximately the same value as the value obtained by culturing the cells without transportation. It was found that the instruments had sufficient stability in practical use.

TABLE 1

| | Villin1 | PEPT1 | P-gp | FABP2 | LGR5 | CDX2 | CYP3A4 | ISX | ALB | AFP |
|---|---|---|---|---|---|---|---|---|---|---|
| Type | 239 | 108 | 204 | 105 | 26 | 282 | 6 | 667 | 165 | 222 |
| Transportation | 221 | 102 | 171 | 151 | 27 | 174 | 10 | 439 | 175 | 269 |
| Caco-2 | 320 | 32 | 259 | 3 | 125 | 290 | | 177 | 100 | 100 |
| Adult Intestin (AI) | 100 | 100 | 100 | 100 | 100 | 100 | 100 | 100 | 0 | 0 |
| Adult Liver (AL) | 6 | 10 | 34 | 0 | 20 | | 1040 | | 25225 | 0 |

EXPLANATION OF REFERENCES

1: pressing plate (holding member) (upper)

11: culture medium

12: cell

13: culture film

17: outer storage container upper lid

19: bolt

2: well plate lid

3: expiration sheet (ventilation sheet)

4: gel sheet (flexible material sheet main body)

41: hole

41A: hole

41*c*, 41*d*: hole

41*e*, 41*f*: part of hole

42: flexible material sheet

5: cell culture insert (cell storage container)

51: opening portion of cell culture insert

6: well plate
61: well (recess)
63: upper side wall portion
7: pressing plate (holding member) (lower)
77: outer storage container with crimp locking tool
77a: crimp locking tool
9: step
10, 20: cell preservation or transportation instrument
P1: internal region
P2: external region
Y: spacer for adjusting height

What is claimed is:

1. A cell preservation or transportation instrument comprising:
a plurality of cell storage containers;
a plate which has a plurality of recesses for holding the plurality of cell storage containers therein; and
a flexible material sheet which seals upper opening portions of the plurality of cell storage containers and upper side wall portions formed by side walls of the recesses of the plate and allows ventilation between an inside and an outside of the plurality of cell storage containers,
wherein the flexible material sheet includes a flexible material sheet main body on a side of the cell storage containers and an expiration sheet having a ventilation property on a side opposite to the side of the cell storage containers,
the flexible material sheet main body has holes for ventilation between the inside and the outside of the plurality of cell storage containers, and
the expiration sheet has waterproofness with a water repellency of 5 kPa or greater in conformity with Japanese Industrial Standard L 1092 and a ventilation property with a Gurley air permeability of 30 sec/100 cm³ or less in conformity with Technical Association of the Pulp and Paper Industry Gurley air resistance test method T460.

2. The cell preservation or transportation instrument according to claim 1,
wherein a diameter of each of the holes provided on the flexible material sheet main body is in a range of 1 mm to 8 mm.

3. The cell preservation or transportation instrument according to claim 1,
wherein the holes of the flexible material sheet main body are provided such that
(1) at least one hole is provided inside the opening portion of the cell storage container, and
(2) at least one hole is provided outside the upper opening portion of the cell storage container and inside an upper opening portion of the recess of the plate by which the cell storage container is held.

4. The cell preservation or transportation instrument according to claim 1,
wherein the holes of the flexible material sheet main body are provided such that at least one hole is provided to straddle between (1) the inside the opening portion of the cell storage container and (2) the outside the upper opening portion of the cell storage container and the inside an upper opening portion of the recess of the plate by which the cell storage container is held.

5. The cell preservation or transportation instrument according to claim 1,
wherein the flexible material sheet or a flexible material sheet main body is a gel sheet.

6. The cell preservation or transportation instrument according to claim 1,
wherein the flexible material sheet or a flexible material sheet main body has an Asker C hardness of 40 degrees or less in conformity with HIS Japanese Industrial Standard K 7312.

7. The cell preservation or transportation instrument according to claim 1,
wherein the flexible material sheet or a flexible material sheet main body has a thickness of 1 mm or greater and 5 mm or less.

8. The cell preservation or transportation instrument according to claim 1,
wherein a bottom portion of the cell storage container is formed of a film having micropores.

9. The cell preservation or transportation instrument according to claim 1, further comprising:
a holding member which holds the plurality of cell storage containers, the plate, and the flexible material sheet in a state of compression in a thickness direction.

10. The cell preservation or transportation instrument according to claim 9,
wherein the holding member includes a set of pressing plates and a plurality of bolts.

11. The cell preservation or transportation instrument according to claim 9,
wherein the holding member includes an outer storage container, an outer storage container upper lid, and a crimp locking unit that crimps and locks the outer storage container and the outer storage container upper lid.

12. A cell transportation method comprising:
transporting the cell preservation or transportation instrument according to claim 1, in which cells are stored in at least some of the plurality of cell storage containers.

* * * * *